United States Patent [19]

Leuenberger et al.

[11] Patent Number: 5,221,735
[45] Date of Patent: Jun. 22, 1993

[54] CYCLODEXTRIN-POLYENE INCLUSION COMPLEXES

[75] Inventors: Bruno Leuenberger, Basle; Hansjörg Stoller, Reinach, both of Switzerland

[73] Assignee: Hoffmann-La Roche Inc., Nutley, N.J.

[21] Appl. No.: 837,292

[22] Filed: Feb. 14, 1992

[30] Foreign Application Priority Data

Feb. 25, 1991 [CH] Switzerland ............... 556/91

[51] Int. Cl.$^5$ .................. C07G 3/00; C07H 15/00
[52] U.S. Cl. ...................... 536/4.1; 536/46; 536/103
[58] Field of Search ............. 536/1.1, 46, 103

[56] References Cited

U.S. PATENT DOCUMENTS

| | | | |
|---|---|---|---|
| 4,054,736 | 10/1977 | Hayashi et al. | 536/103 |
| 4,524,068 | 6/1985 | Szejtli et al. | 536/103 |
| 4,883,785 | 11/1989 | Chow et al. | 536/6.5 |
| 4,886,788 | 12/1989 | Skuballa et al. | 536/103 |
| 5,007,966 | 4/1991 | Hedges et al. | 536/103 |
| 5,043,326 | 8/1991 | Stadler née Szoke et al. | 536/103 |

FOREIGN PATENT DOCUMENTS

| | | |
|---|---|---|
| 392608 | 10/1990 | European Pat. Off. . |
| 050167 | 2/1959 | Fed. Rep. of Germany . |
| 3815902 | 11/1989 | Fed. Rep. of Germany . |
| 198675 | 9/1987 | Japan . |
| 267261 | 11/1987 | Japan . |
| 2162529 | 2/1986 | United Kingdom . |
| 200251 | 2/1982 | World Int. Prop. O. . |
| 910739 | 11/1989 | World Int. Prop. O. . |

*Primary Examiner*—Nathan M. Nutter
*Attorney, Agent, or Firm*—George M. Gould; William H. Epstein; Catherine R. Roseman

[57] ABSTRACT

Inclusion complexes of the polyenes apocarotenal and lycopene in a cyclodextrin as well as their manufacture are described. The inclusion complexes are soluble in water, alcohol or water/alcohol mixtures.

4 Claims, No Drawings

CYCLODEXTRIN-POLYENE INCLUSION COMPLEXES

BACKGROUND

Vitamins and especially carotenoids are generally insoluble in polar solvents, especially water. However, it is desirable for most applications that these compounds should be present in a soluble form in such solvents. This is of particular importance to achieve a high bioavailability of these compounds as active ingredients. It is also important in exploiting the colouring power of carotenoids which is of great interest for the colouring of foodstuffs. Therefore, the formation of cyclodextrin inclusion complexes with vitamins or carotenoids is of particular interest for conferring solubility in polar solvents.

Attempts have been made to formulate carotenoids in polar solvents. The carotenoids may be dissolved in an oil phase and/or in an organic solvent and processed with water to form an emulsion. In another process a carotenoid is ground in an oil and the resulting suspension is then emulsified in water to produce an emulsion.

These formulations have the disadvantage that they are turbid in water, since the suspension or emulsion consists of particles or light-scattering droplets. In such suspensions and emulsions the active ingredients are usually present as particles having a size of 0.1 to 10 $\mu$m. Also, such suspensions or emulsions of carotenoids do not have lasting stability. Further, the carotenoids are readily decomposed by the action of heat and light.

Cyclodextrins are known to form inclusion complexes soluble in polar solvents with a large number of compounds. However, cyclodextrins have not been successfully used to make the carotenoid 62 -carotene soluble in a polar solvent.

In Japanese published Kokai 26 72 61, $\beta$-carotene is mixed together with a cyclodextrin. However, solutions are not obtained. Rather, suspensions ar formed which again separate upon standing.

SUMMARY

In accordance with this invention, we have made the unexpected discovery that the carotenoids apocarotenal and lycopene when combined with cyclodextrin form complexes. These new complexes, surprisingly, can be dissolved in polar solvents.

Therefore, the present invention provides inclusion complexes, soluble in a polar solvent, of apocarotenal or lycopene with a cyclodextrin, and methods for their manufacture.

DETAILED DESCRIPTION

Complexes are obtained in accordance with the invention by bringing a cyclodextrin into contact with apocarotenal and/or lycopene in a polar solvent. Any method of contacting the cyclodextrin with lycopene or apocarotenal and polar solvent may be used in accordance with this invention. For example, a) dissolving a cyclodextrin in a polar solvent and treating this solution with apocarotenal or lycopene, or
b) dissolving apocarotenal or lycopene in an organic solvent, dissolving a cyclodextrin in a polar solvent, and bringing both solutions together, or
c) intensively mixing solid apocarotenal or solid lycopene with a cyclodextrin in the presence of a small amount of water, and subsequently bringing this mixture together with a polar solvent.

Process a) is the preferred embodiment. Inclusion complexes are herein designated as complexes. Any conventional method for producing complexes is suitable for purposes of this invention.

$\alpha$-, methyl $\beta$-, and hydroxypropyl $\beta$-cyclodextrins ar preferable cyclodextrins. In particular, for the manufacture of inclusion complexes which contain apocarotenal, there are preferably used $\beta$-cyclodextrins, especially methyl $\beta$-cyclodextrin or hydroxypropyl $\beta$-cyclodextrin, with methyl $\beta$-cyclodextrin being especially preferred. $\alpha$-Cyclodextrin is preferably used for the manufacture of inclusion complexes which contain lycopene. However, any cyclodextrin may be used according to this invention.

Any polar solvent may be used for the purposes of the invention. An example of a polar solvent is a solvent in which cyclodextrin is soluble. Polar solvents and methods for determining solubility are well known in the art. Water or a lower alkyl alcohol or a mixture of water and a lower alkyl alcohol is preferably used as the polar solvent. Water is especially suitable as the polar solvent.

In the case of mixtures, the volume ratio between water and the lower alkyl alcohol is conveniently about 1:30 to about 10:1. As lower alkyl groups of the aforementioned lower alkyl alcohols there come into special consideration alkyl groups which contain up to 6 carbon atoms and which are straight-chain or branched. The lower alkyl alcohol is preferably methanol, ethanol or n-propanol, especially methanol or ethanol.

Any amounts of said components may be used in this invention. In particular, the cyclodextrin can be added to about an 8-fold to 10-fold amount of distilled water, lower alkyl alcohol or mixture of water and lower alkyl alcohol and dissolved at a temperature of bout 5° C. to 90° C. This is preferably carried out in a temperature range of about 20° C. to 60° C. The apocarotenal or lycopene is added to this solution, with the amount of polyene, i.e. apocarotenal or lycopene, used conveniently corresponding to about 1/10 to 1/10,000 of the amount of cyclodextrin used. The weight ratio between polyene and cyclodextrin is preferably about 1:10 to about 1:200.

In accordance with b) the apocarotenal or lycopene as an about 8-12% solution, especially as an about 10% solution, in an organic solvent can be added to the solution of cyclodextrin in a polar solvent such as water, with chloroform or hexane as particular organic solvents. The organic solvent is removed in a second step, e.g. by distillation. Distillation and other methods of solvent removal are known in the art. Any organic solvent may be used. An example of an organic solvent is an organic solvent in which lycopene and/or apocarotenal are soluble. Organic solvents and methods for determining solubility are well known in the art.

Alternatively, in accordance with c) apocarotenal and lycopene in solid form can be mixed intensively with about a 10-fold to 12-fold amount of cyclodextrin in the presence of a small amount of water. Subsequently, this mixture can be brought together with a polar solvent. Any solid constituents which may be present are removed according to usual methods known in the art, for example by filtration.

In forming the complexes, the temperature used is not critical. Any temperature may be used in accordance with this invention. In particular, the procedure is carried out in a temperature range of about 5° C. to about 90° C., with a temperature range of about 20° C. to about 60° C. being especially preferred. The mixture is stirred for about 20 minutes to about 70 minutes to evaporate any solvent present, and subsequently filtered in order to separate any solid constituents from the solution. The filtration can be carried out a room temperature or at an elevated temperature. Filtration is preferably carried out after cooling the solution to room temperature. Filtration methods are well known in the art.

The inclusion complex formed from apocarotenal and cyclodextrins such as methyl β-cyclodextrin can be isolated in solid form by evaporating the solvent and can subsequently be redissolved. This procedure can be repeated at will without noticeable changes occurring.

Particular advantages of inclusion complexes in accordance with the invention over the previously known cyclodextrin/polyene formulations are as follows:

1) formation of true solutions in water or water/alcohol mixtures, which permits the manufacture of stable and turbidity-free solutions and gives rise to a substantially improved bioavailability because the polyene is present in the form of a molecular dispersion,
2) enlargement of colour range,
3) increase of stability of the included polyenes to heat and light.

The invention is illustrated in more detail, but not limited in any way, by the following Examples:

EXAMPLE 1

5.0 g of methyl β-cyclodextrin (static methylated β-cyclodextrin having about 1.8 $CH_3$ groups per anhydroglucose unit) are dissolved in 40 ml of water at a temperature of 60° C. 0.5 g of crystalline apocarotenal is added to this solution. The mixture is heated to 55° C. and stirred at this temperature for 20 minutes. After cooling to room temperature the solid constituents are filtered off from the deep red solution.

The spectrophotometric measurement of this solution gives an apocarotenal content of 0.16 mg per ml of solution.

The aqueous solution of the apocarotenal-cyclodextrin complex is converted into a solid powder using a laboratory spray-dryer. The powder obtained exhibits good solubility in cold water and again gives an aqueous solution upon the addition of water.

The solution of the apocarotenal-cyclodextrin complex in water and a solution of the same concentration of apocarotenal in hexane are left to stand in daylight for 10 days. The apocarotenal/hexane solution fades to a pale orange solution, while the aqueous solution of the apocarotenal-cyclodextrin complex shows no colour change.

EXAMPLE 2

5.0 g of hydroxypropyl β-cyclodextrin (about 0.6 $CH_3CH(CH_3)$ O groups per anhydroglucose unit) are mixed with 0.3 g of apocarotenal and moistened with about 1 ml of water. The mixture is kneaded at room temperature for 3 hours, subsequently added to 40 ml of water at room temperature and freed from solid constituents by filtration. The resulting clear, dark red solution contains 3 μg of apocarotenal per ml of solution.

EXAMPLE 3

5.0 g of α-cyclodextrin are dissolved in 40 ml of water at a temperature of 60° C. 0.3 g of lycopene dissolved in 4 ml of chloroform is added to this mixture. This suspension is heated to 60° C. and stirred for a further 20 minutes, whereby the chloroform is evaporated. After cooling the solution to room temperature all solid constituents are filtered off. The resulting dark yellow solution contains 2 μg of lycopene per ml.

We claim:
1. Complexes of a polyene selected from the group consisting of lycopene and apocarotenal with cyclodextrin.
2. The complexes of claim 1, wherein the cyclodextrin is α-cyclodextrin, methyl β-cyclodextrin or hydroxypropyl β-cyclodextrin.
3. The complexes of claim 2, wherein the cyclodextrin is α-cyclodextrin and the polyene is lycopene.
4. The complexes of claim 2, wherein the cyclodextrin is methyl β-cyclodextrin or hydroxypropyl β-cyclodextrin and the polyene is apocarotenal.

* * * * *